United States Patent
Luchterhandt et al.

(10) Patent No.: US 6,835,271 B1
(45) Date of Patent: Dec. 28, 2004

(54) ADHESIVE SYSTEMS

(75) Inventors: Thomas Luchterhandt, Krailling (DE); Hendrik M Grupp, Utting (DE); Rainer Guggenberger, Herrsching (DE)

(73) Assignee: 3M Espe AG, Seefeld (DE)

( * ) Notice: Subject to any disclaimer, the term of this patent is extended or adjusted under 35 U.S.C. 154(b) by 287 days.

(21) Appl. No.: 10/048,848

(22) PCT Filed: Jul. 28, 2000

(86) PCT No.: PCT/EP00/07323

§ 371 (c)(1),
(2), (4) Date: Apr. 5, 2002

(87) PCT Pub. No.: WO01/10389

PCT Pub. Date: Feb. 15, 2001

(30) Foreign Application Priority Data

Aug. 6, 1999 (DE) .......................... 199 37 092

(51) Int. Cl.⁷ ................................ A61K 6/00
(52) U.S. Cl. .................... 156/272.2; 156/327; 523/116; 523/118
(58) Field of Search ............................. 156/272.2, 327; 523/115, 116, 118

(56) References Cited

U.S. PATENT DOCUMENTS 6,147,136 A  *  11/2000  Bissinger .................... 523/116

FOREIGN PATENT DOCUMENTS

| DE | 196 48 283 A1 | 5/1998 | |
|----|---------------|--------|---|
| EP | 0 712 622 A1 | 5/1996 | |
| EP | 712622 A1 * | 5/1996 | ............ A61K/6/00 |
| EP | 0 897 710 A2 | 2/1999 | |
| WO | 98/46197 A1 | 10/1998 | |
| WO | 00/56800 A1 | 9/2000 | |

* cited by examiner

*Primary Examiner*—Blaine Copenheaver
*Assistant Examiner*—John T. Haran
(74) *Attorney, Agent, or Firm*—Birch, Stewart, Kolasch & Birch, LLP

(57) ABSTRACT

The invention relates to the use of adhesive systems which are radically polymerizable and contain 1–30 wt.-% of a reactive solvent with a pKS value less than or equal to that of acetone and are used for the attachment of materials which are only or also cationically polymerizable to hard tissue containing water. The adhesive systems contain at least one component i) which is capable of starting a radical reaction and one component ii) which contains radically polymerizable monomers which are acid-functional or contain groups which can form acids and optionally customary additives.

13 Claims, No Drawings

ADHESIVE SYSTEMS

This application is the national phase under 35 U.S.C. § 371 of PCT International Application No. PCT/EP00/07323 which has an International filing date of Jul. 28, 2000, which designated the United States of America.

The present invention relates to adhesive systems for the attachment of materials which are only or also cationically polymerizable.

To date, predominantly methacrylate and acrylate monomers have been used in polymerizable dental compositions. The 2,2-bis[4-(2-hydroxy-3-methacryloyloxypropoxy) phenyl]-propane (bis-GMA) [U.S. Pat. No. 3,066,112] described by Bowen deserves particular attention. Mixtures of this methacrylate with triethylene glycol dimethacrylate also still serve today as the standard formulation for dental plastic direct filling materials. Methacryl derivatives of twice-formylated bis-(hydroxymethyl)tricyclo[5.2.1.0$^{2,6}$] decane have also proved successful as monomers for dental composites [W. Gruber et al., DE-A-27 14 538; W. Schmitt et al., DE-A-28 16 823; J. Reiners et al., EP 0 261 520]. A major disadvantage of these dental compositions is however the high volume shrinkage which occurs through the polymerization. This can be minimized for example through the use of ring-opening monomers, such as the cationically curing epoxides.

Only a little is known about cationically curable epoxide compositions for dental applications. U.S. Pat. No. 5,556,896 describes epoxide-containing compositions which must necessarily contain spiroorthocarbonates as shrinkage-compensating monomers. Bowen describes a composition containing quartz sand and an aliphatic diepoxide (bisphenol-A-diglycidyl ether) which in the cured state allegedly displays good stability in the mouth environment [J. Dent. Res. 35, 1956, 360–379]. AT-A-204 687 describes epoxide dental compositions based on bisphenol-A which are cured by means of Lewis acid catalysts. The specifications DE-A-196 48 283, WO-96/13538 and WO-95/30402 likewise describe polymerizable dental compositions based on epoxides and their use.

Although there are extensive experiences with epoxides and cycloaliphatic epoxides (U.S. Pat. No. 2,716,123, U.S. Pat. No. 2,750,395, U.S. Pat. No. 2 863 881, U.S. Pat. No. 3,187,018), such monomers and cationically polymerizable compositions formulated therefrom with the properties necessary for dental applications have not been commercially available at any point in time.

This is because the curing of these cationically polymerizable compositions is inhibited by water and the hard tooth substance, for example in dentine, contains approx. 11 to 16 weight per cent water (G.-H. Schumacher et. al., Anatomie und Biochemie der Zähne, Gustav Fischer Verlag, 1990, 4$^{th}$ edition).

Thus it is readily explicable that for example formulations of dental filling materials on an epoxides basis, in contrast to formulations on a (meth)acrylate basis, cannot show any inherent adhesion to dentine and the use of such materials was thus not possible.

For improved attachment of (meth)acrylate-based dental filling materials—i.e. radically curing systems—so-called adhesive systems are used.

The quality of these adhesive systems is reflected in the following criteria:
Complete bonding to the hard tooth substance without flaws ("sealing"),
Complete bonding to the filling material,
Permanent bond.

However, as the polymerization of (meth)acrylate systems takes place via a radical mechanism, a bonding of cationically polymerizing tooth materials to such adhesive systems is not to be expected. A dental adhesive system for (also) cationically cross-linking materials has not been commercially available on the market at any point in time.

Although DE-A-197 43 564 describes compositions based on solvent-free, cationically and/or radically curable cross-linking systems as radiation-curable adhesion promoters—so-called primers—these are used only for the coating of anhydrous materials, for example plastics such as polyvinylidene chloride (PVDC) or silicon.

WO-98/47046 describes photopolymerizable epoxide-based mixtures containing an epoxide resin, an iodonium salt, a transfer molecule sensitive in visible light and an electron donor, and their use as a dental adhesive system. However, it has been shown that with such mixtures, no bonding to cationically curing mixtures is to be achieved on the hard tooth substance (see comparison mixtures 1 to 3).

WO-99/34766 states that compositions with a high proportion of cationically curable groups do not bond at all, or only very poorly, to hard tooth tissue. To solve the problem, it is proposed to provide either a hybrid composition containing constituents with radically and cationically polymerizable groups or a composition which is largely free from cationically polymerizable groups.

The object of the present invention is to provide methods of bringing either materials which are only cationically cross-linking or materials which are radically and cationically cross-linking to bond to hard tissue containing water, such as a tooth, the bonding preferably being intended to take place essentially uniformly over the entire surface available for the bonding.

This object is achieved according to the invention by the use of adhesive systems which are radically polymerizable and contain 1 to 30 wt.-%, preferably not more than 20 wt.-% and in a particularly preferred manner not more than 15 wt.-% of a reactive solvent with a pKS value less than or equal to that of acetone, for the attachment of materials which are only or also cationically polymerizable to hard tissue containing water, the adhesive system containing at least one component i) which is capable of starting a radical reaction, and one component ii) which contains radically polymerizable monomers which are acid-functional or contain groups which can form acids.

Surprisingly, it was found that in the case of the use of radically polymerizable adhesive systems and cationically polymerizable dental materials, a good bonding to hard tissue containing water, such as hard tooth substance, can be achieved, although there are two completely different polymerization forms.

As the cationic polymerization takes place via an ionic chain propagation mechanism, there are theoretically no possibilities of polymerizing non-radically polymerizing monomers with radically growing chains.

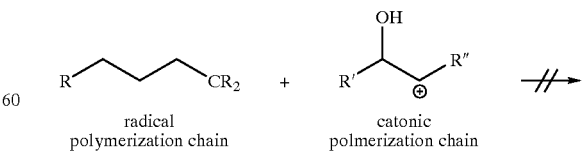

radical polymerization chain + catonic polmerization chain

In addition, the water contained in the hard tissue or the reactive solvent added to the adhesive system should disturb the cationic polymerization, as it acts as a chain-breaking agent. Through the continuous chain breaking, many short chains should thus form which prevent the construction of a polymer network.

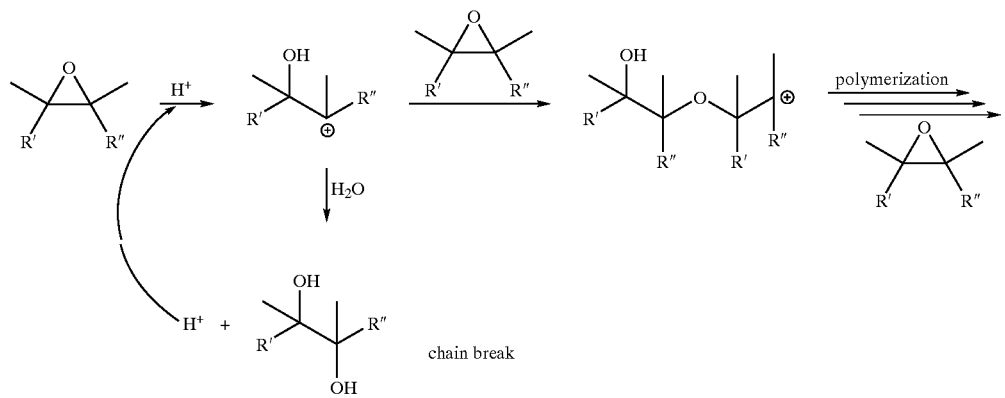

chain break

It is completely surprising that, despite what has been said above, cationically polymerizable materials can be brought to bond to the hard tooth substance containing water or also to radically polymerizing adhesive systems containing reactive solvents. Further advantages are the lower toxicity compared with customary solvents such as $CH_2Cl_2$ or acetonitrile, and the reduced volatility which allows the adhesive mixture to be applied uniformly before the solvent evaporates. Improved solution properties which allow the use of a large number of different monomers are also advantageous.

The invention is described in more detail in the following.

The adhesive mixture which displays the described advantages when used according to the invention contains as constituent i) preferably 0.01 to 10 wt.-%, in particular 0.1 to 7 wt.-%, and particularly preferably 0.1 to 5 wt.-% of an initiator system which is capable of starting a radical polymerization and as constituent ii) preferably 90 to 99.99 wt.-%, in particular 93 to 99.90 wt.-% and particularly preferably 95 to 99.90 wt.-% of the radically polymerizable material.

The proportion of reactive solvent lies in the range from 1 to 30 wt.-%, preferably in the range from 5 to 25 wt.-% and quite particularly preferably in the range from 8 to 20 wt.-%.

Reactive solvents are those with acid protons and a pKS value of less than or equal to that of acetone, such as water, methanol, ethanol, n- and i-propanol. In tests, it has been shown that such solvents, in particular those which carry hydroxyl groups, contrary to what was said above, improve the bond between cationic materials and radically polymerizing materials.

The radical-forming initiators which can be contained as component i) in the mixtures are described in the literature (e.g. J.-P. Fouassier, Photoinitiation, Photopolymerization and Photocuring, Hanser Publishers, Munich, Vienna, New York, 1995 or else J.-P. Fouassier, J. F. Rabek (Publ.), Radiation Curing in Polymer Science and Technology, Vol. II, Elsevier Applied Science, London, New York, 1993). They can also be substances activatable by UV or visible light, such as benzoin alkyl ethers, benzil ketals, acylphosphinic oxides or aliphatic and aromatic 1,2-diketone compounds, for example camphorquinone, the catalyst activity being able to be accelerated through the addition of activators, such as tertiary amines, for example dialkylamino-4-benzoic acid ester, or organic phosphites, in per se known manner.

Suitable initiator systems for the triggering of the radical polymerization via a redox mechanism are for example the peroxide/amine, peroxide/barbituric acid derivatives or peroxide/acids systems. When using such initiator systems it is expedient to keep an initiator (e.g. peroxide) and a catalyst component (e.g. amine) separate. The two components are then mixed together homogeneously shortly before their use.

The customary monomers used in radically curing dental materials can be used as component ii), component ii) having to contain 3 to 100 wt.-% radically polymerizable monomers which are acid-functional, or contain groups which can form acids with water, such as for example acid chlorides or anhydrides, there being meant by acids mono-, di- or polycarboxylic acids with the following radicals: $C_1$ to $C_{25}$ alkyl or cycloalkyl radicals optionally substituted with N, O, S, Si, P or halogen, aromatic $C_6$ to $C_{12}$ radicals or heterocyclic $C_3$ to $C_{12}$ radicals substituted with N, O, S, P and optionally with halogen. In just the same way, acids such as 4-methacryloxy-ethyl trimellitic acid or its anhydrides (Takeyama, M. et al., J.Jap.Soc. f. Dent. App. A. Mat. 19, 179 (1978)) or the reaction products of trimellitic acid chloride anhydride can be used with aminic, thiolic or hydroxylic (meth)acrylic acid esters, such as for example 2-hydroxyethylene methacrylate (HEMA) or methacroyloxy-ethyl-o-phthalate.

Other preferred acids are unsaturated organic esters of monofluorophosphonic acids, as described in U.S. Pat. No. 3,997,504, unsaturated organic esters of acids of phosphorus which contain chlorine or bromine directly bound to the phosphorus, as described in EP-A-0 058 483, unsaturated organic esters of phosphoric acid which are present as cyclic pyrophosphates (anhydrides) as described in DE-A-3 048 410 and unsaturated organic esters of phosphoric or phosphonic acids as described in DE-A-2 711234 and DE-A-3 150 285. Just as preferred are the hydrolysis-stable, polymerizable acrylic phosphonic acids of DE-A-1 974 670 8.

Quite particularly preferred are ethylenically unsaturated carboxylic acids of the formula:

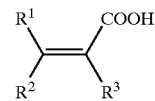

in which:
$R^1$, $R^2$, $R^3$=H, $C_1$ to $C_{25}$ alkyl or cycloalkyl radicals, optionally substituted with N, O, S, Si, P or halogen, or aromatic $C_6$ to $C_{12}$ radicals or heterocyclic $C_3$ to $C_{12}$ radicals containing N, O, S, P and optionally substituted with halogen, as well as ethylenically unsaturated phosphoric acid esters of the following formula:

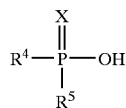

in which:

X=O, S;

$R^4$ and $R^5$ independently of each other stand for H, OH or $C_1$ to $C_{25}$ alkyl or cycloalkyl, optionally substituted or bridged with heteroatoms such as N, halogen, Si, O or S, aromatic $C_6$ to $C_{12}$ and/or heterocyclic $C_4$ to $C_{12}$ radicals, or substituted with acrylic acid esters, the radicals $R^4$ and $R^5$ also independently of each other being able to be bound to the phosphorus via O, or

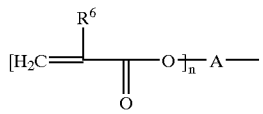

where $R^6$ stands for hydrogen or $C_1$ to $C_6$ alkyl, n is an integer $\geq 1$ and A is a divalent $C_1$ to $C_{25}$ alkylene or cycloalkylene radical, optionally substituted or bridged with N, O, S, Si, P or halogen, or an aromatic $C_6$ to $C_{12}$ radical, and/or heterocyclic $C_4$ to $C_{12}$ radical with N, O, S, or P and optionally substituted with halogen, provided that the group which contains the radical $R^6$ is present at least once.

Typical monomers or prepolymers which cure according to the radical chain mechanism and can also be present in component ii) are acrylates or methacrylates. Suitable are mono- and polyfunctional (meth)acrylate monomers. Typical representatives of this compound class (see DE-A-4 328 960) are alkyl(meth)acrylates, including the cycloalkyl (meth)acrylates, aralkyl(meth)acrylates and 2-hydroxyalkyl (meth)acrylates, for example hydroxypropyl methacrylate, hydroxyethyl methacrylate, isobornyl acrylate, isobornyl ethacrylate, butylglycol methacrylate, acetylglycol methacrylate, triethylene glycol methacrylate, polyethylene glycol dimethacrylate, 2-phenylethyl ethacrylate, 2-ethylhexyl ethacrylate, cyclohexyl methacrylate, lauryl methacrylate and hexanediol di(meth)acrylate.

Long-chained monomers as described in U.S. Pat. No. 3,066,112 based on bisphenol-A and glycidyl methacrylate or their derivatives produced by the addition of isocyanates can also be used. Also suitable are compounds of the type bisphenyl-A-diethyloxy (meth)acrylate and bisphenol-A-dipropyloxy (meth)acrylate. The oligoethoxylated and oligopropoxylated bisphenol-A-diacrylic and dimethacrylic acid esters can also be used. Also well suited are the diacrylic and dimethacrylic acid esters of bis(hydroxymethyl)-tricyclo[$5.2.1.0^{2,6}$]-decane named in DE-A-2 816 823 and the diacrylic and dimethacrylic acid esters of the compounds of the bis(hydroxymethyl)-tricyclo [$5.2.1.0^{2,6}$]-decane extended with 1 to 3 ethylene oxide and/or propylene oxide units. Mixtures of the named monomers can also be used.

The adhesive systems according to the invention can also contain fillers, dyes, flow modifiers, stabilizers, solvents, ion-emitting substances, bactericidal or antibiotic substances which contain X-ray-opacity-increasing compounds or further modifiers.

Suitable as fillers are for example substances such as are used in customary dental materials, particularly preferably quartz, aerosils, highly-dispersed silicic acids, organic fillers or glasses, such as are used in composites customary on the market, or mixtures of these substances or also those such as are described in DE-A-196 48 283 A1 (page 10, lines 48–59).

Of the ion-emitting substances, those are preferred which make possible the release of fluoride ions, such as fluoride salts of the first or second main groups, such as sodium fluoride or calcium fluoride, or complex fluoride salts, such as. $KZnF_3$, or such as are described in EP-A-0 717 977, fluoride-emitting glasses, as well as mixtures of these fluoride ion sources.

There can be used as bactericidal or antibiotic substances, for example, chlorohexidine, pyridinum salts or the customary pharmaceutical substances, such as β-lactam antibiotics (penicillins), cephalosporins, tetracyclins, ansamycins, kanamycins, chloroamphenicol, fosfomycin, antibacterial macrolides, polypeptide antibiotics, chemotherapeutics, such as sulphonamides, dihydrofolate reductase inhibitors, nitrofuran derivatives or gyrasis inhibitors.

The adhesive mixtures according to the invention can also contain diluents, preferably solvents such as dialkyl ketones (e.g. acetone, methyl ethyl ketone), acetylacetone or alcohols (e.g. ethanol, propanol) or also thin-flowing polymerizable substances such as 2-hydroxyethyl methacrylate.

There can be used as stabilizers, for example, radical captors such as hydroxybenzenes or HALS (hindered amines light stabilizers).

In addition, at least one non-polymerizable acid can also be contained, such as an unsaturated carboxylic acid, phosphoric acid, phosphonic acid, sulphuric acid, sulphinic acid, sulphenic acid, mineral acid, Lewis acid or complex acid, such as for example $H_2PtCl_6$.

If the adhesive mixtures contain additives in addition to the components i) and ii), these can be present individually or mixed in the quantities of 0.1 wt.-% to 85 wt.-%, the mixture being prepared such that with the components i) and ii) they add up to 100 wt.-% in total.

The adhesive mixture comprises for example the following constituents:

i) a radical initiator system in a quantity of 1 to 5 wt.-%;
ii) radically polymerizable monomers which are acid-functional or contain groups which can form acids, in a quantity of 3 to 99 wt.-%;
iii) radically polymerizable monomers which are not acid, in a quantity of 0 to 90 wt.-%;
iv) solvents in a quantity of 1 to 75 wt.-%;
v) a reactive solvent in a quantity of 1 to 30 wt.-%;
vi) fillers in a quantity of 0 to 75 wt.-%;
vii) bactericidal substances or preservatives in a quantity of 0 to 20 wt.-%;
viii) ion-emitting substances in a quantity of 0 to 25 wt.-%;
ix) stabilizers in a quantity of 0 to 10 wt.-%;
x) non-polymerizable acids in a quantity of 0 to 25 wt.-%.

The instant invention also comprises a kit comprising a) an adhesive slustem, containing a component i), which is capable of starting a radical reaction and a component ii), which contains radically polymerizable monomers, which are acid-functional or contain groups, which can form acids, iii) 1 to 30 wt.-% of a receive solvent with a pKS value less than or equal to that of acetone an b) a material which is only or also cationically polymerizable. Moreover, the kit optionally has component iii) stored separately from the other components of the kit.

In the following, the invention is explained in more detail by means of examples, these to be understood as being embodiments and not limiting in any way.

Bonding Measurement on Bovine Teeth Through Adhesive Attachment of a Filling Material:

The adhesion bond was tested by a peel-off test on bovine teeth. Per test, 5 freshly extracted bovine teeth were ground down by means of sand paper until there was a sufficiently large exposed dentine surface. Wax platelets with a punched-out hole measuring 6 mm were glued onto each of these surfaces to obtain a standardized bonding surface. The further treatment of the test surface and the application of the adhesive mixture were in each case as indicated in the preparation examples.

Preparation of a Cationically Curing Filling Material:

In a three-finger kneader, the following constituents are kneaded into a homogeneous paste. There are used for 100 g paste:

- 75.000 wt.-% (75.000 g) quartz (average grain size 0.9 μm, was silanized with 5 wt.-% glycidyloxypropyltrimethoxysilane);
- 0.525 wt.-% (0.525 g) 4-methylphenyl-4-isopropylphenyl-iodoniumtetrakis-(pentafluorophenyl)borate;
- 0.223 wt.-% (0.223 g) camphorquinone (Merck, Darmstadt);
- 0.001 wt.-% (0.001 g) ethyl-4-dimethylaminobenzoate (Merck, Darmstadt);
- 0.001 wt.-% (0.001 g) 2-butoxyethyl-4-dimethylaminobenzoate;
- 12.125 wt.-% (12.125 g) 3,4-epoxycyclohexyl-3,4-epoxycyclohexane carboxylate;
- 12.125 wt.-% (12.125 g) 1,3,5,7-tetrakis-(2,1-ethanediyl-3,4-epoxycyclohexyl)-1,3,5,7-tetramethylcyclotetrasiloxane.

Preparation of Adhesive Mixture 1 According to the Invention:

For the preparation of 10 g of adhesive mixture 1, the following constituents are mixed together intensively:

- 22.300 wt.-% (2.930 g) 2-hydroxyethyl)-methacrylate (Merck, Darmstadt);
- 7.000 wt.-% (0.700 g) ethanol;
- 1.200 wt.-% (0.120 g) camphorquinone (Merck, Darmstadt);
- 0.900 wt.-% (0.090 g) ethyl-4-dimethylaminobenzoate (Merck, Darmstadt);
- 68.600 wt.-% (6.860 g) 4-methacryloxyethyl trimellitic acid (see U.S. Pat. No. 4,148,988).

Preparation of Adhesive Mixture 2 According to the Invention:

For the preparation of 10 g of adhesive mixture 2, the following constituents are mixed together intensively:

- 19.600 wt.-% (1.960 g) 2-hydroxyethyl methacrylate (Merck, Darmstadt);
- 1.200 wt.-% (0.120 g) camphorquinone (Merck, Darmstadt);
- 0.900 wt.-% (0.090 g) ethyl-4-dimethylaminobenzoate (Merck, Darmstadt);
- 68.300 wt.-% (6.830 g) methacryloyl-oxydecyl-phosphate;
- 10.000 wt.-% (1.000 g) water.

Preparation of Adhesive Mixture 3 According to the Invention:

For the preparation of 10 g of adhesive mixture 1, the following constituents are mixed together intensively:

- 5.500 wt.-% (0.550 g) (2-hydroxyethyl)-methacrylate (Merck, Darmstadt);
- 1.200 wt.-% (0.120 g) camphorquinone (Merck, Darmstadt);
- 0.900 wt.-% (0.090 g) ethyl-4-dimethylaminobenzoate (Merck, Darmstadt);
- 25.000 wt.-% (2.500 g) 4-methacryloxyethyl trimellitic acid (see U.S. Pat. No. 4,148,988).
- 55.000 wt.-% (5.500 g) methacryloyl-oxydecyl-phosphate;
- 12.400 wt.-% (1.240 g) water.

Preparation of Comparison Mixture 1:

For the preparation of 10 g of comparison mixture 1, the following constituents are mixed together intensively:

- 97.300 wt.-% (9.730 g) 1,3,5,7-tetrakis-(2,1-ethanediyl-3,4-epoxycyclohexyl)-1,3,5,7-tetramethylcyclotetrasiloxane;
- 2.0 wt.-% (0.200.9) Rhodorsil PI 2074 (Rhone Poulenc, iodonium salt);
- 0.500 wt.-% (0.50 g) camphorquinone (Merck, Darmstadt);
- 0.200 wt.-% (0.020 g) BEDB (Lambson).

Preparation of Comparison Mixture 2:

For the preparation of 10 g of comparison mixture 2, the following constituents are mixed together intensively:

- 97.300 wt.-% (9.730 g) 3,4-epoxycyclohexyl-3,4-epoxycyclohexane carboxylate;
- 2.0 wt.-% (0.200 9) Rhodorsil PI 2074 (Rhone Poulenc, iodonium salt);
- 0.500 wt.-% (0.050 g) camphorquinone (Merck, Darmstadt);
- 0.200 wt.-% (0.020 g) BEDB (Lambson);

Preparation of Comparison Mixture 3:

For the preparation of 10 g of comparison mixture 3, the following constituents are mixed together intensively:

- 48.650 wt.-% (4.865 g) 3,4-epoxycyclohexylmethyl-3,4-epoxycyclohexane carboxylate;
- 48.650 wt.-% (4.865 g) 1,3,5,7-tetrakis-(2,3-ethanediyl-3,4-epoxycyclohexyl)-1,3,5,7-tetramethylcyclotetrasiloxane:
- 2.000 wt.-% (0.200 g) Rhodorsil PI 2074 (Rhone Poulenc, iodonium salt);
- 0.500 wt.-% (0.050 9) camphorquinone (Merck, Darmstadt);
- 0.200 wt.-% (0.020 9) BEDB (Lambson).

Method:

The test surface was etched for 20 seconds following the procedure customary in practice, using a customary phosphoric acid solution (Atzgel Minitip®, ESPE Dental AG, Seefeld), and then rinsed with water. A quantity of the test mixtures sufficient for complete wetting of the test surface was worked into the thus-prepared dentine surfaces with a microbrush for 20 seconds, blown briefly with compressed air and polymerized for 20 seconds by means of a light-polymerization device (Elipar Highlight®, ESPE). The cationically curing filling material, the preparation of which is described above, was then introduced into the holes of the wax platelets and fully polymerized by 40 seconds' exposure to light. The testpieces were then removed in a tensile test (Zwick Universal Test Machine).

The bonding values measured can be seen in Table 1.

TABLE 1

Bonding of the adhesive mixtures described in the examples:

| Adhesive mixture | Dentine bonding [Mpa]* |
|---|---|
| Adhesive mixture 1 | 3.6 |
| Adhesive mixture 2 | 4.2 |
| Adhesive mixture 3 | 3.8 |
| Pertac Universal Bond (ESPE) | 2.2 |
| Prime & Bond NT (Dentsply) | 1.9 |
| Scotchbond Multi Purpose Plus (3 M) | 2.1 |
| Visio Bond (ESPE) | 0.0 |
| Comparison mixture 1 | 0.0 |
| Comparison mixture 2 | 0.0 |
| Comparison mixture 3 | 0.0 |

*Average from 5 measurements each

The above table shows that with the cationically polymerizing comparison mixtures 1 to 3, no bonding to the hard tooth substance containing water can be achieved. On the other hand, it is shown that with the radically polymerizing adhesive mixtures 1 to 3 according to the invention and also with the shown radically polymerizing commercially available adhesive systems according to the invention, cationically polymerizable dental materials can be adhesively attached to a given substance.

What is claimed is:

1. A method of attaching materials which are cationically polymerizable on hard tissue containing water, the method comprising using an adhesive system to join the material to the hard tissue; the adhesive system is radically polymerizable and contains 1 to 30 wt.-% of at least one reactive solvent with a pKS value less than or equal to that of acetone, the adhesive system containing at least one component i) which is capable of starting a radical reaction, and at least one component ii) which contains 3 to 100 wt.-% radically polymerizable monomers which are acid-functional or contain groups which can form acids.

2. The method according to claim 1, wherein the reactive solvent carries hydroxyl groups.

3. The method according to claim 1, component i) being present in proportions from 0.01 to 10 wt.-% and component ii) in proportions of 90.00 to 99.99 wt.-%.

4. The method according to claim 1, the materials being dental materials and the hard tissue a tooth.

5. The method according to claim 1, the adhesive system containing as component ii) a singly or repeatedly ethylenically unsaturated organic acid or its anhydride or its acid chloride.

6. The method according to claim 1, wherein the adhesive system also contains one or more of the following components selected from the group consisting of: a further radical and/or cationic polymerization initiator; a diluent, a filler such as is used in customary dental materials; a fluoride ion source; an acid which contains no double bond; and a bactericidal agent or customary antibiotic.

7. The method according to claim 6, wherein the diluent is an organic solvent customary in adhesive mixtures or a thin-flowing compound which contains radically polymerizable groups.

8. The method according to claim 1, the adhesive system being polymerized through the supply of electromagnetic radiation.

9. The method according to claim 8, wherein electromagnetic radiation is irradiation with light of a wavelength from 350 to 1000 nm.

10. The method according to claim 1, component ii) containing an ethylenically unsaturated carboxylic acid of the following formula:

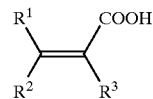

in which:
$R^1$, $R^2$, $R^3$=H, $C_1$ to $C_{25}$ alkyl or cycloalkyl radicals, optionally substituted with N, O, S, Si, P or halogen, or aromatic $C_6$ to $C_{12}$ radicals or heterocyclic $C_3$ to $C_{12}$ radicals with N, O, S, P and optionally substituted with halogen, or contains an ethylenically unsaturated phosphoric acid ester of the following formula:

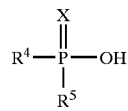

in which:
X=O, S;
$R^4$ and $R^5$ independently of each other stand for H, OH or $C_1$ to $C_{25}$ alkyl or cycloalkyl, optionally substituted or bridged with heteroatoms, such as N, halogen, Si, O or S, aromatic $C_6$ to $C_{12}$ and/or heterocyclic $C_4$ to $C_{12}$ radicals, or substituted with acrylic acid esters, the radicals $R^4$ and $R^5$ also independently of each other being able to be bound to the phosphorus via O, or

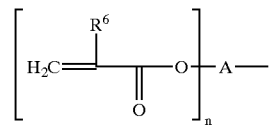

where
$R^6$ stands for hydrogen or $C_1$ to $C_6$ alkyl,
n is an integer $\geq 1$ and
A is a divalent $C_1$ to $C_{25}$ alkylene or cycloalkylene radical, optionally substituted or bridged with N, O, S, Si, P or halogen, or an aromatic $C_6$ to $C_{12}$ radical, and/or heterocyclic $C_4$ to $C_{12}$ radical with N, O, S, or P and optionally substituted with halogen, provided that the group which contains the radical $R^6$ is present at least once.

11. The method according to claim 1, whereby the hard tissue is a hard tooth substance and after applying the adhesive system and before joining the material to the hard tooth substance, coating is carried out with another material which is only or also cationically polymerizable.

12. Kit comprising a) an adhesive system, containing a component i), which is capable of starting a radical reaction and a component ii), which contains radically polymerizable monomers, which are acid-functional or contain groups, which can form acids, iii) 1 to 30 wt.-% of a reactive solvent with a pKS value less than or equal to that of acetone and b) a material which is only or also cationically polymerizable.

13. Kit according to claim 12, component iii) being stored separately from the other components.

* * * * *

UNITED STATES PATENT AND TRADEMARK OFFICE
CERTIFICATE OF CORRECTION

PATENT NO.    : 6,835,271 B1
DATED         : December 28, 2004
INVENTOR(S)   : Luchterhandt, Thomas It is certified that error appears in the above-identified patent and that said Letters Patent is hereby corrected as shown below:

Column 2,
Line 58, delete "  " and insert --  --, therefor.

Line 61, delete "catonic" and insert -- cationic --, therefor.
Line 62, delete "polmerization" and insert -- polymerization --, therefor.

Column 6,
Line 59, delete "slustem" and insert -- system --, therefor.
Line 63, delete "receive" and insert -- reactive --, therefor.
Line 64, delete "an" and insert -- and --, therefor.

Column 8,
Line 21, delete "(0.200.9)" and insert -- (0.200 g) --, therefor.
Line 32, delete "(0.200 9)" and insert -- (0.200 g) --, therefor.
Line 50, delete "(0.050 9)" and insert -- (0.050 g) --, therefor.
Line 52, delete "(0.020 9)" and insert -- (0.020 g) --, therefor.

Column 9,
Line 52, after "diluent" delete "," and insert -- ; --, therefor.

Signed and Sealed this

Twenty-fifth Day of October, 2005

JON W. DUDAS
*Director of the United States Patent and Trademark Office*